United States Patent [19]
Tabak

[11] Patent Number: 4,560,537
[45] Date of Patent: Dec. 24, 1985

[54] MULTISTAGE PROCESS FOR CONVERTING OXYGENATES TO HYDROCARBONS

[75] Inventor: Samuel A. Tabak, Wenonah, N.J.

[73] Assignee: Mobil Oil Corporation, New York, N.Y.

[21] Appl. No.: 641,245

[22] Filed: Aug. 16, 1984

Related U.S. Application Data

[62] Division of Ser. No. 548,377, Nov. 3, 1983, Pat. No. 4,482,772.

[51] Int. Cl.$^4$ .............................................. B01J 8/04
[52] U.S. Cl. ...................................... 422/190; 208/49
[58] Field of Search ............... 585/254, 255, 531, 314, 585/315, 322, 407, 330, 517, 533, 304, 413, 415, 640, 319, 489, 639; 196/46; 208/138, 255, 71, 49, 135; 55/48; 422/116, 190, 189, 141, 142, 201

[56] References Cited

U.S. PATENT DOCUMENTS

| | | | |
|---|---|---|---|
| 3,928,483 | 12/1975 | Chang et al. | 208/135 X |
| 3,960,978 | 6/1976 | Givens et al. | 585/531 |
| 4,025,576 | 5/1977 | Chang et al. | 585/322 |
| 4,058,576 | 11/1977 | Chang et al. | 422/201 X |
| 4,150,062 | 4/1979 | Garwood et al. | 208/71 X |
| 4,211,640 | 7/1980 | Garwood et al. | 208/255 |
| 4,357,147 | 11/1982 | Bezman | 585/330 X |
| 4,379,123 | 4/1983 | Daviduk et al. | 422/142 |
| 4,387,261 | 6/1983 | Chester et al. | 585/489 |
| 4,393,265 | 7/1983 | Bonifaz | 585/639 |

*Primary Examiner*—Richard L. Chiesa
*Attorney, Agent, or Firm*—A. J. McKillop; M. G. Gilman; L. G. Wise

[57] ABSTRACT

An integrated system is provided for converting methanol or the like to heavy hydrocarbon products, especially distillate range hydrocarbons. In a first stage catalytic process oxygenate feedstock is converted to lower olefins. Byproduct aromatics are passed through a second stage oligomerization reactor with olefins. Distillate range hydrocarbons are recovered and hydrotreated to provide an improved fuel product.

10 Claims, 4 Drawing Figures

MULTISTAGE PROCESS FOR CONVERTING OXYGENATES TO HYDROCARBONS

This is a division of copending application Ser. No. 548,377, filed on Nov. 3, 1983, and now U.S. Pat. No. 4,482,772.

BACKGROUND OF THE INVENTION

This invention relates to an integrated system for converting oxygenates, such as methanol or dimethyl ether (DME), to liquid hydrocarbons. In particular it provides a continuous process for producing distillate range fuel products by dehydrating the oxygenate feedstock catalytically to produce an intermediate lower olefinic stream, oligomerizing the olefins to produce distillate/gasoline, and hydrogenating the distillate product to provide a stabilized product for use as diesel fuel or the like.

Recent developments in zeolite catalysts and hydrocarbon conversion processes have created interest in utilizing olefinic feedstocks, for producing $C_5+$ gasoline, diesel fuel, etc. In addition to the basic work derived from ZSM-5 type zeolite catalysts, a number of discoveries have contributed to the development of a new industrial process, known as Mobil Olefins to Gasoline/Distillate ("MOGD"). This process has significance as a safe, environmentally acceptable technique for utilizing feedstocks that contain lower olefins, especially $C_2$-$C_5$ alkenes. This process may supplant conventional alkylation units. In U.S. Pat. Nos. 3,960,978 and 4,021,502, Plank, Rosinski and Givens disclose conversion of $C_2$-$C_5$ olefins, alone or in admixture with paraffinic components, into higher hydrocarbons over crystalline zeolites having controlled acidity. Garwood et al have also contributed improved processing techniques to the MOGD system, as in U.S. Pat. Nos. 4,150,062, 4,211,640 and 4,227,992. The above-identified disclosures are incorporated herein by reference.

Conversion of lower olefins, especially propene and butenes, over HZSM-5 is effective at moderately elevated temperatures and pressures. The conversion products are sought as liquid fuels, especially the $C_5+$ aliphatic and aromatic hydrocarbons. Olefinic gasoline is produced in good yield by the MOGD process and may be recovered as a product or recycled to the reactor system for further conversion to distillate-range products. Operating details for typical MOGD units are disclosed in copending U.S. Pat. No. 4,456,779 and U.S. Pat. No. 4,433,185, incorporated herein by reference.

In addition to their use as shape selective oligomerization catalysts, the medium pore ZSM-5 type catalysts are useful for converting methanol and other lower aliphatic alcohols or corresponding ethers to olefins. Particular interest has been directed to a catalytic process for converting low cost methanol to valuable hydrocarbons rich in ethene and $C_3+$ alkenes. Various processes are described in U.S. Pat. Nos. 3,894,107 (Butter et al), 3,928,493 (Chang et al), 4,025,571 (Lago), and in copending U.S. patent application Ser. No. 388,768, filed June 15, 1982 (Yurchak et al) and now abandoned. Significance of the methanol-to-olefins ("MTO") type processes, especially for producing ethene, is discussed in *Hydrocarbon Processing*, November 1982, pp. 117-120. It is generally known that the MTO process can be optimized to produce a major fraction of $C_2$-$C_4$ olefins; however, a significant $C_5+$ byproduct is coproduced, including polymethylbenzenes, such as durene, as described in U.S. Pat. No. 4,025,576 (Chang et al). Prior process proposals have included a separation section to recover ethene and other gases from byproduct water and $C_5+$ hydrocarbon liquids. Treatment of the $C_5+$ liquids to dealkylate the polymethylbenzenes has been necessary to convert this fraction to satisfactory liquid fuel, for instance as disclosed in U.S. Pat. No. 4,347,397 (Dwyer et al) and U.S. Pat. No. 4,387,261 (Chester et al). Such post treatment processes add significantly to the cost of liquid fuels plant.

SUMMARY OF THE INVENTION

It has been discovered that methanol, DME or the like may be converted to liquid fuels, particularly distillate, in a multi-stage continuous process, with integration between the major process units. The initial stage MTO type process hydrocarbon effluent stream, after byproduct water separation, can be fed directly to the MOGD section without prior fractionation or treatment of heavier hydrocarbons. In particular, it has been found that durene-containing $C_5+$ hydrocarbons can be fed to the oligomerization unit with lower olefins. Heavy aromatics are passed through with the MOGD distillate product, which may be post-hydrogenated to saturate the olefinic components and hydrogenate aromatics. This hydrotreated distillate product thus obtained has a high cetane number and excellent properties for diesel fuel, jet fuel or the like.

In a preferred embodiment, the invention provides an integrated continuous process for converting oxygenated organic feedstock to liquid hydrocarbons comprising methods and apparatus for contacting feedstock with at least two primary stage dehydration catalyst comprising ZSM-5 type catalyst at elevated temperature and moderate pressure to convert at least a portion of the feedstock to hydrocarbons containing a major fraction of $C_2$-$C_4$ olefins and a minor fraction containing $C_5+$ heavy hydrocarbons; cooling and separating dehydration effluent to provide an aqueous liquid stream, a heavy hydrocarbon liquid stream and a light hydrocarbon vapor stream rich in $C_2$-$C_4$ olefins; pressurizing and heating at least a portion of the olefinic light hydrocarbon stream and substantially all of the heavy hydrocarbon liquid stream to form a secondary stage olefinic feedstream; contacting the olefinic feedstream in a secondary stage with oligomerization catalyst comprising medium-pole shape selective acidic zeolite at substantially increased pressure and moderate temperature to convert olefins to a heavier liquid hydrocarbon effluent stream comprising olefinic gasoline and distillate range liquids; fractionating the liquid hydrocarbon oligomerization effluent stream to obtain a distillate stream, olefinic stream and lighter hydrocarbon stream; recycling at least a portion of the olefinic gasoline stream to the secondary stage oligomerization step; and hydrogenating olefinic distillate to provide a stabilized distillate product.

Other objects and features of the invention will be seen in the following description and drawings.

THE DRAWINGS

DESCRIPTION OF PREFERRED EMBODIMENTS

Catalyst versatility permits the same zeolite to be used in both the primary dehydration stage (MTO) and secondary oligomerization stage (MOGD). While it is within the inventive concept to employ substantially different catalysts in these stages, it is advantageous to employ a standard ZSM-5 having a silica alumina molar ratio of 70:1.

The oligomerization catalysts preferred for use herein include the crystalline aluminosilicate zeolites having a silica to alumina ratio of at least 12, a constraint index of about 1 to 12 and acid cracking activity of about 160–200. Representative of the ZSM-5 type zeolites are ZSM-5, ZSM-11, ZSM-12, ZSM-22, ZSM-23, ZSM-35 and ZSM-38. ZSM-5 is disclosed and claimed in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,979. Also, see U.S. Pat. No. 3,832,449 for ZSM-12; U.S. Pat. No. 4,076,842 for ZSM-23; U.S. Pat. No. 4,016,245 for ZSM-35 and U.S. Pat. No. 4,046,839 for ZSM-38. The disclosures of these patents are incorporated herein by reference. A suitable catalyst for fixed bed operation is HZSM-5 zeolite with 35 wt.% alumina binder in the form of cylindrical extrudates of about 1–5 mm.

These medium pore shape selective catalysts are sometimes known as porotectosilicates or "Pentasil" catalysts. Other catalysts and processes suitable for converting methanol/DME to lower olefins are disclosed in U.S. Pat. No. 4,393,265 (Bonifaz), U.S. Pat. No. 4,387,263 (Vogt et al.) and European Patent Application No. 0081683 (Marosi et al.), and ZSM-45. In addition to the preferred aluminosilicates, the borosilicate, ferrosilicate and "silicalite" materials may be employed. ZSM-5 type catalysts are particularly advantageous because the same material may be employed for dehydration of methanol to DME, conversion to lower olefins and oligomerization.

In this description, metric units and parts by weight are employed unless otherwise stated. While various reactor configurations may be used, including fluidized bed catalytic reactors, moving bed and fixed bed reactors, the invention is described for use in a plurality of fixed bed reactors operated under differing process conditions depending upon relative position in the system.

Figure 1:
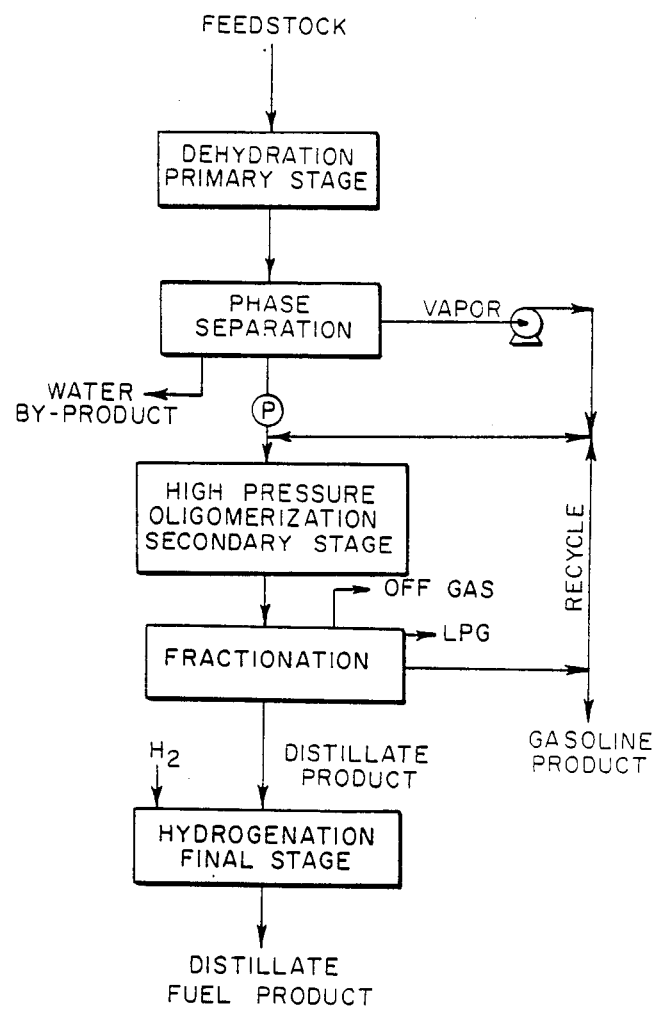
FIG. 1 is a process flow sheet showing the major unit operations and process streams.

Referring to FIG. 1, the process feedstock (methanol or DME, for instance) is fed to the primary stage where it is converted to a lower olefin and gasoline hydrocarbon plus water by dehydration of the oxygenated feedstock. Byproduct water is recovered by simple phase separation from the cooled effluent. Liquid hydrocarbons consisting essentially of $C_5^+$ gasoline range materials are pumped to the higher secondary stage pressure. This stream may contain as much as 6 to 10 wt.% durene. At least a portion of the vapor phase effluent from the primary stage is compressed and heated along with the liquids to oligomerization reaction temperature, and the combined olefinic stream (optionally containing recycled olefinic gasoline) is reacted at high pressure and elevated temperature over the catalyst. Secondary stage effluent is then separated into light gases, $C_5^+$ gasoline for recycle in part and distillate range hydrocarbons. The distillate stream contains a major fraction of high boiling aliphatics and a minor amount of aromatics. Hydrotreating (HDT) in the final stage is a relatively mild process to saturate the olefinic compounds and convert the aromatics to corresponding naphthenes without substantial cracking or dealkylation to yield a distillate fuel product. Ethylene (ethene, $C_2H_2$) may be recovered as a valuable chemical feedstock from the process.

In the process for catalytic conversion of olefins to heavier hydrocarbons by catalytic oligomerization using an acid crystalline zeolite, such as ZSM-5 type catalyst, process conditions can be varied to favor the formation of either gasoline or distillate range products. At moderate temperature and relatively high pressure, the conversion conditions favor distillate range product having a normal boiling point of at least 165° C. (330° F.). Lower olefinic feedstocks containing $C_2$–$C_6$ alkenes may be converted selectively; however, the distillate mode conditions do not convert a major fraction of ethylene. While propene, butene-1 and others may be converted to the extent of 50 to 95% in the distillate mode, only about 10 to 50% of the ethylene component will be consumed. Accordingly, the ethene is advantageously recovered prior to the secondary oligomerization stage, as shown in FIG. 2, which depicts a preferred system for converting methanol ($CH_3OH$) and/or DME.

In the primary stage ethene production may be optimized by employing fixed bed primary stage conditions in the temperature range of about 260° C. to 425° C., a pressure range of about 170 to 800 kPa and weight hourly space velocity range of about 0.5 to 1.0 based on ZSM-5 equivalent catalyst and methanol equivalent in the primary stage feedstock. Typically about 25 to 90% of MeOH/DME feedstock is converted per reactor pass and water diluent is cofed with methanol and/or dimethyl ether in a molar ratio of about 0.1:1 to 5:1. Under these conditions, the primary stage hydrocarbon effluent usually contains about 25 to 40 wt.% ethene, about 10 to 50 wt.% propene, about 2 to 30 wt.% butene, less than 10 wt.% $C_1$ to $C_4$ paraffins, and about 5 to 20 wt.% aromatics, including about 1 to 5 wt.% durene.

Figure 2:
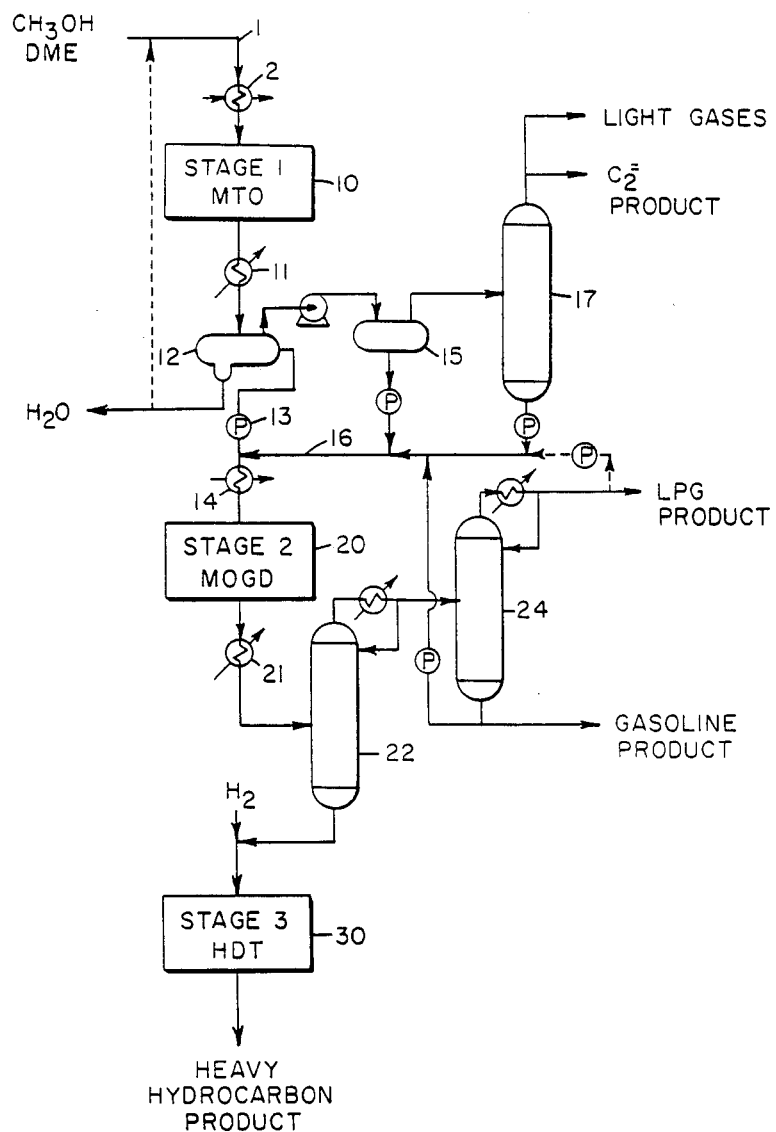
FIG. 2 is a schematic representation of a preferred multi-stage reactor system and fractionation system for ethane recovery.

In the preferred embodiment of FIG. 2, the feedstock is methanol, which may be partially dehydrated in a separate process step over gamma-alumina catalyst to yield dimethyl ether (DME) and water. A preliminary dewatering step can be used to provide a feedstock consisting essentially of $CH_3OH$ and/or DME; however, the presence of water in the MTO reactor may be beneficial. The feedstock is fed continuously under low pressure through line 1, and heat exchange 2 where it is raised to process temperature and introduced to the first stage MTO reactor system 10. The first stage effluent is cooled in exchanger 11 to condense water and a major amount of $C_5^+$ hydrocarbons. These liquids are separated from the hydrocarbon vapor in phase separator means 12. Byproduct water may be recovered from unreacted feedstock and discarded or a portion may be recycled.

The liquid hydrocarbon phase from separator 12 is then brought up to distillate mode oligomerization pressure by pump 13, heated in exchanger 14 and introduced to the secondary stage reactor system 20. The ethene-rich hydrocarbon vapor stream from separator 12 is compressed and condensed liquid, mainly $C_3$–$C_4$ olefin, is separated in high pressure separator 15, after which it is pumped to secondary stage pressure and combined through conduit 16 with other hydrocarbon liquids. Ethene product and other $C_2^-$ light gases are recovered from the vapor stream by fractionator unit 17, which may be a cryogenic still or the like. Methane and ethane offgas may be removed from the system at this point.

Pressurized $C_3^+$ hydrocarbons from fractionator 17 are combined with other hydrocarbon liquid streams through conduit 16 and passed to the second stage MOGD reactor system 20 under high pressure at moderate temperature. As discussed hereafter, the preferred MOGD reactor system is a multizone arrangement. Second stage effluent is cooled in heat exchanger 21 and fractionated in distillation tower 22, from which the distillate range liquids boiling above about 165° to 175° C. (330° F.) are fed as a continuous stream to the third stage HDT reactor 30. Gasoline, rich in $C_5^+$ olefins and lighter hydrocarbons are further fractionated in tower 24 to provide an olefinic gasoline stream for recycle to the MOGD reactor system or recovered as product. The lighter hydrocarbons, rich in $C_3$-$C_4$ alkenes may be condensed and recovered as LPG product or optionally recycled to the MOGD reactor system.

The main concept is to cascade substantially all $C_3^+$ hydrocarbon first stage product into an MOGD reactor followed by hydrotreating of the distillate product. This will minimize the number of process steps and will maximize distillate production by polymerizing gasoline range olefins, and by alkylating gasoline range aromatics. Durene will be reduced via saturation to its corresponding naphthene in the hydrotreating step.

A typical MTO operation is conducted over a fixed bed of HZSM-5/alumina extrudate catalyst at about 170 kPa (25 psia), with a 1:1 $H_2O:CH_3OH$ equivalent ratio at 315° C. (600° F.) at a space velocity (WHSV=0.5-1) to convert about 50% of the oxygenated organic feedstock components to hydrocarbons. Table A lists the organic product distribution from a typical MTO run.

TABLE A

| MTO Product Distribution | |
|---|---|
| Component | wt. % |
| Temperature, °F. | 600 |
| Methane, wt. % | 0.6 |
| Ethylene, wt. % | 26.2 |
| Ethane, wt. % | 0.1 |
| Propylene, wt. % | 22.8 |
| Propane | 3.9 |
| Butenes | 7.9 |
| Isobutane | 3.9 |
| n-Butane | 2.6 |
| Pentenes | 2.4 |
| $C_5$ P + N | 7.1 |
| $C_6$ P + N | 5.1 |
| $C_7$ O | 0.6 |
| $C_7$ P + N | 3.2 |
| $C_7$ O | 0.7 |
| $C_8$ P + O + N | 2.1 |
| $C_9$ P + O + N | 1.3 |
| $C_{10}$ P + O + N | 1.1 |
| Benzene | 0.1 |
| Toluene | 0.5 |
| $C_8$ Aromatics | 3.5 |
| $C_9$ Aromatics | 2.1 |
| $C_{10}$ Aromatics | 2.2 |
| Durene | 1.7 |

Figure 3:
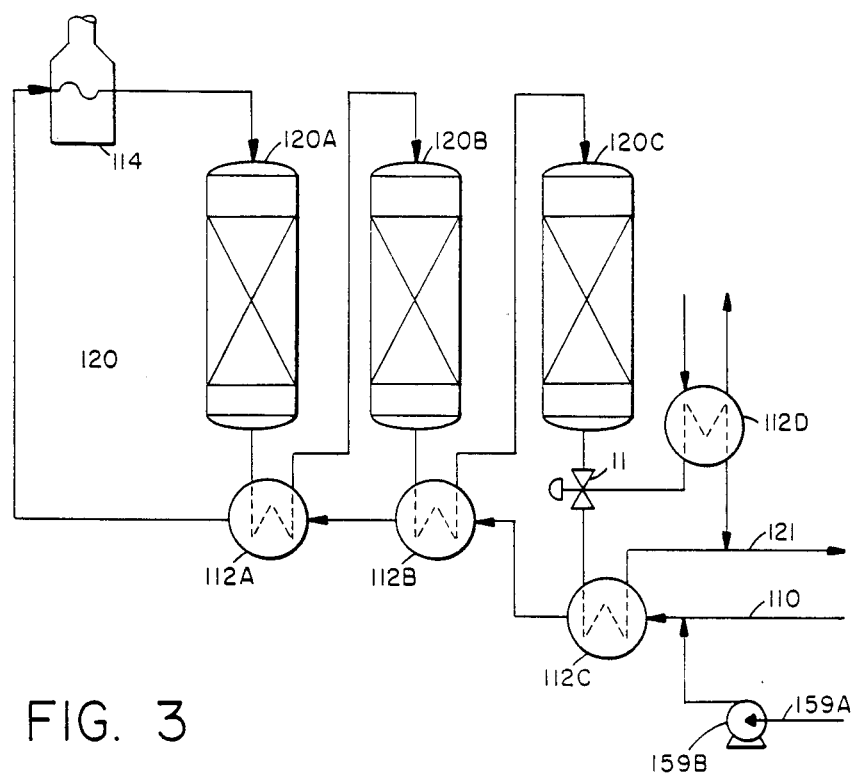
FIG. 3 is a typical olefin conversion reactor system for distillate mode operation.

A typical distillate mode secondary stage reactor system 120 is shown in FIG. 3. A plural reactor system may be employed with inter-reactor cooling, whereby the reaction exotherm can be carefully controlled to prevent excessive temperature above the normal moderate range of about 190° to 315° (375°-600° F.). The olefinic feedstream is introduced through conduit 110 and carried by a series of conduits through heat exchangers 112A, B, C and furnace 114 where the feedstream is heated to reaction temperature. The olefinic feedstock is then carried sequentially through a series of zeolite beds 120A, B, C wherein at least a portion of the olefin content is converted to heavier distillate constituents. Advantageously, the maximum temperature differential across only one reactor is about 30° C. ($\Delta T \sim 50°$ F.) and the space velocity (LHSV based on olefin feed) is about 0.5 to 1.5. The heat exchangers 112A and 112B provide inter-reactor cooling and 112C reduces the effluent to separation temperature. An optional heat exchanger 112D may further recover heat from the effluent stream 121 prior to separation. Gasoline from recycle conduit 159A is pressurized by pump means 159B and combined with the feedstream, preferably at a ratio of about 1-3 parts by weight per part of olefin in the secondary stage feedstream.

Preferably, the secondary stage process conditions are optimized to produce heavy liquid hydrocarbons having a normal boiling point greater than about 175° C., and employs a fixed bed of ZSM-5 type catalyst to oligomerize olefins at a start of cycle temperature of about 230° C. to 260° C. and pressure of about 4200 to 7000 kPa.

Rather than recover ethene and other light gases from the first stage effluent, ethene can be sent to the MOGD (FIG. 4), it will pass through relatively unreacted, thus reducing the amount of $C_3^+$ in the ethylene separation plant and improving its efficiency.

Figure 4:
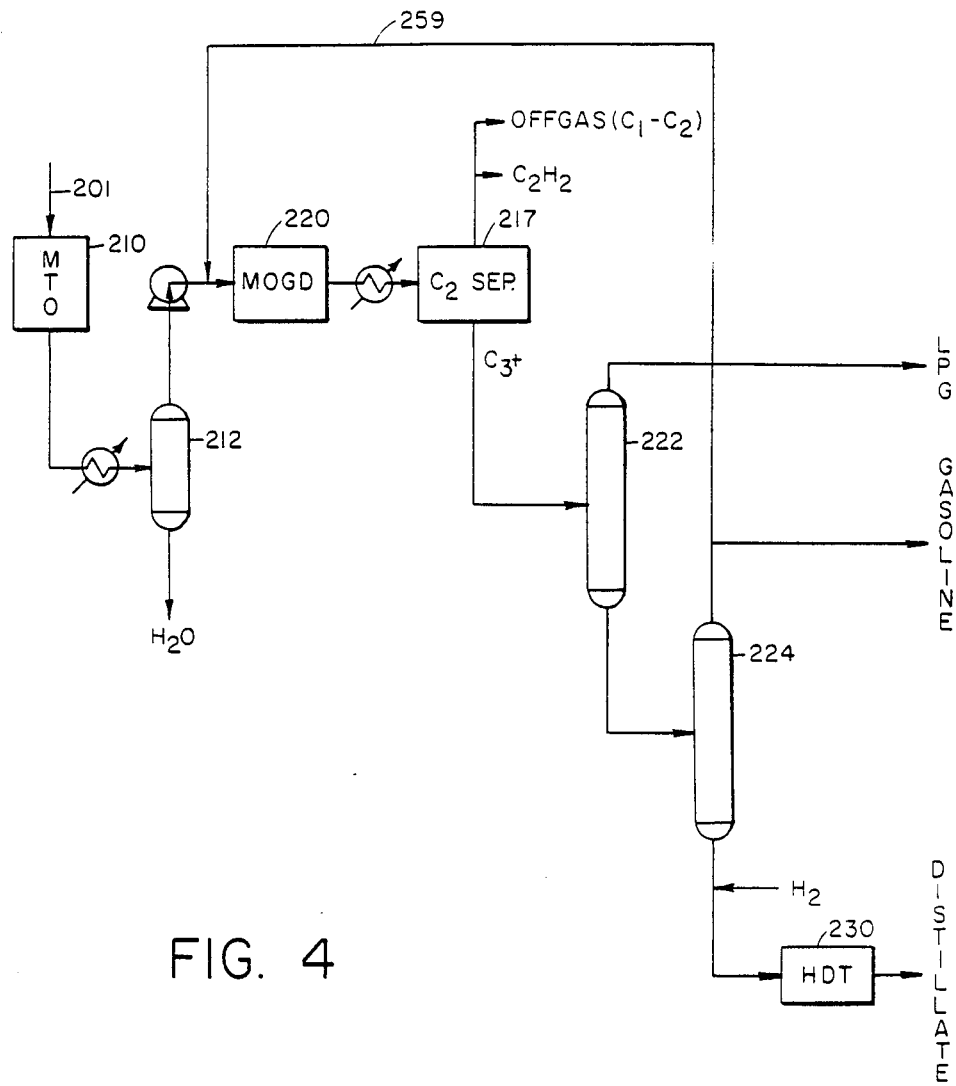
FIG. 4 is a schematic representation of an alternative system.

An alternative system depicted schematically in FIG. 4, provides for passing oxygenate feedstock 201 through the primary stage 210, followed by water separation unit 212 and cascading substantially the entire organic effluent to the secondary stage 220, operating in maximum distillate mode. Unreacted ethene and other light gases (e.g. methane and ethane) are recovered by deethanizer unit 217 and the $C_3^+$ hydrocarbons are fractionated first in a debutanizer unit 222 and splitter tower 224. Olefinic gasoline is recovered as product and partially recycled through line 259 to the MOGD reactor 220. The distillate range bottoms stream is hydrogenated to stabilize the olefinic components and reduce polyalkylbenzenes to naphthenes. This results in distillate yield being increased by polymerization of the $C_5^+$ olefins (which normally go to gasoline), and by aromatic/olefin alkylation in the MOGD reactor. Gasoline end point is also lowered to send the durene to the product hydrotreater 230. The durene (along with other heavy aromatics) is then saturated to tetramethylcyclohexane, thus eliminating the need for a dealkylation unit. The aromatic saturation will also increase the cetane value of the distillate product.

The hydrogenation step may employ a hydrogenation catalyst comprising Group VIIIA and Group VIA (IUPAC) metals under mild hydrotreating conditions to convert durene to a naphthene compound and to saturate olefinic components. Preferred catalyst comprises Co or Ni together with W or Mo, and/or noble metals, such as Pt, Pd. A suitable HDT process is described by Garwood and Lee in U.S. Pat. No. 4,211,640, incorporated in reference. Similar hydrogenation processes adapted for continuous operation are known in petroleum refining technology.

While the primary stage dehydration reactor has been exemplified herein by a fixed bed unit, a suitable fluid catalyst apparatus is disclosed in U.S. Pat. No. 4,379,123 (Daviduk and Haddad).

As compared to a conventional system wherein MTO liquids containing gasoline range materials and durene are recovered and severely hydrotreated to reduce the durene content by dealkylation, the present system is an economic process for increasing the relative amount of distillate. Typically, an increase of 40% or more of high quality fuel can be achieved. The amount of aromatics in the gasoline is likewise decreased from about 22% to 15%. The preferred distillate mode operation can provide a larger part of the total fuel products as heavy hydrocarbons, usually in a distillate/gasoline ratio of about 1.3 to 6:1, while retaining a high yield of valuable ethylene product. Substantially all of the polymethylbenzenes or other aromatics formed in the dehydration reactor stage are accumulated in the distillate fraction according to the present invention, and the hydrotreated distillate durene content is decreased substantially below 2 wt.%, preferably below 1%.

The present process is particularly useful in producing a major product stream wherein the 175° C.+ fraction consists mainly of $C_{10}$ to $C_{20}$ aliphatic hydrocarbons containing a minor amount of cyclic components. The low temperature, high pressure distillate mode secondary stage operation favors the formation of linear oligomers.

By integration of dehydration, oligomerization and hydrotreating, a route is provide for converting MTC products to distillate with a minimum of processing steps. This technique will reduce capital cost and provide an economic process for production of distillate fuels and ethene, with gasoline and LPG being made in minor amount.

Various modifications can be made to the system, especially in the choice of equipment and non-critical processing steps. While the invention has been described by specific examples, there is no intent to limit the inventive concept as set forth in the following claims.

I claim:

1. A continuous multi-stage catalytic system for converting oxygenated feedstock to liquid hydrocarbons comprising
   primary stage catalytic means containing dehydration catalyst for converting oxygenate to olefinic and aromatic hydrocarbons;
   interstage separation means for recovering water from the primary stage effluent stream;
   means for pressurizing and heating primary stage hydrocarbon effluent stream rich in $C_3$+ components;
   secondary stage catalytic oligomerization reactor means containing medium pore shape selective zeolite oligomerization catalyst for converting said olefinic hydrocarbons in the primary stage effluent stream to liquid hydrocarbons comprising a major amount of distillate in the presence of aromatic hydrocarbons;
   fractionation means for separating secondary stage effluent into a light hydrocarbon stream rich in $C_3$–$C_4$ aliphatic hydrocarbons, a $C_5$+ gasoline stream and distillate range stream;
   means for recycling at least a portion of the $C_5$+ gasoline stream to the secondary stage for combining with substantially the entire primary stage $C_3$+ hydrocarbon stream; and
   hydrotreating reactor means for catalytically hydrogenating olefinic and aromatic components of the distillate stream to provide a stabilized distillate product.

2. An integrated continuous system for converting oxygenated organic feedstock to liquid hydrocarbons comprising:
   first reactor means for contacting feedstock with at least one primary stage acidic zeolite conversion catalyst at elevated temperature and moderate pressure to convert at least a portion of the feedstock to hydrocarbons containing a major fraction of $C_2$–$C_{14}$ olefins and a minor fraction containing $C_5$+ heavy hydrocarbons;
   means for cooling and separating reactor effluent from the primary stage to provide an aqueous liquid stream, a heavy hydrocarbon liquid stream and a light hydrocarbon vapor stream rich in $C_2$–$C_4$ olefins;
   means for pressurizing and heating at least a portion of the olefinic light hydrocarbon stream and substantially all of the heavy hydrocarbon liquid stream to form a secondary stage olefinic feedstream;
   second reactor means for contacting the olefinic feedstream in a secondary stage with oligomerization catalyst comprising medium-pore shape selective acidic zeolite at substantially increased pressure and moderate temperature to convert olefins to a heavier liquid hydrocarbon effluent stream comprising olefinic gasoline and distillate range liquids;
   separation means for fractionating the liquid hydrocarbon effluent stream from the secondary stage to obtain an olefinic distillate stream, olefinic gasoline stream and lighter hydrocarbon stream;
   means for recycling at least a portion of the olefinic gasoline stream to the second reactor means; and
   third reactor means for catalytically hydrogenating the olefinic distillate to provide a stabilized distillate product.

3. The system of claim 2 further comprising means for fractionating hydrocarbon dehydration effluent to recover an ethene-rich gas stream and an olefinic stream rich in $C_3$+ olefins.

4. The system of claim 2 wherein the oligomerization catalyst comprises ZSM-5 type zeolite.

5. The system of claim 4 wherein the primary stage and secondary stage catalysts consist essentially of HZSM-5.

6. The system of claim 2 further comprising means for cooling the primary stage reactor effluent under process pressure; means for compressing light hydrocarbon vapors to form a second liquid hydrocarbon stream to be fed under process pressure to the secondary stage.

7. The system of claim 2 further comprising means for compressing and fractionating light hydrocarbon vapor separated from the primary stage reactor effluent.

8. The system of claim 2 comprising a fixed bed primary stage having means for maintaining a pressure range of about 170 to 800 kPa and weight hourly space velocity range of about 0.5 to 1.0, whereby ethene production is optimized.

9. The system of claim 2 comprising means for recovering and recycling primary stage water diluent for cofeeding with feedstock in a molar ratio of about 0.1:1 to 5:1.

10. Apparatus for converting a lower aliphatic alcohol or derivative thereof to liquid hydrocarbon product comprising a primary stage reactor containing zeolite dehydration conversion catalyst and means for maintaining said reactor conditions for producing lower olefins, a minor amount of liquid hydrocarbons and by-product water;

phase separation means for cooling and recovering water, liquid hydrocarbons and light olefinic hydrocarbon vapor from the primary stage effluent;

pump means for pressurizing and passing substantially all of said liquid hydrocarbons from the primary stage to a secondary stage oligomerization reactor containing a shape selective medium pore acid zeolite catalyst;

compressor means for pressurizing and passing at least a portion of light olefinic hydrocarbons from the phase separation means to the secondary stage reactor;

means for heating said pressurized stream to second stage oligomerization temperature under conditions for producing a major amount of olefinic distillate range hydrocarbons;

means for fractionating second stage effluent to recover gasoline range olefinic liquid, distillate range olefinic liquid and light gas;

pump means for recycling at least a portion of the gasoline liquid to the secondary stage reactor, and a final stage hydrotreating reactor containing hydrogenation catalyst for mild hydrotreating of the olefinic distillate to produce a paraffinic distillate product.

* * * * *

UNITED STATES PATENT AND TRADEMARK OFFICE
CERTIFICATE OF CORRECTION

PATENT NO. : 4,560,537
DATED : December 24, 1985
INVENTOR(S) : S. A. Tabak It is certified that error appears in the above-identified patent and that said Letters Patent is hereby corrected as shown below:

Col. 1, line 60, "3,928,493" should be --3,928,483--.

Col. 2, line 35, "two" should be --one--.

Col. 2, line 49, "medium-pole" should be --medium-pore--.

Col. 2, line 55, insert --gasoline-- after "olefinic".

Col. 8, line 15, "$C_2-C_{14}$" should be --$C_2-C_4$--.

Col. 10, line 3, "Secondary" should be --Second--.

Col. 10, line 5, "Second" should be --Secondary--.

Signed and Sealed this
Eighteenth Day of November, 1986

*Attest:*

DONALD J. QUIGG

*Attesting Officer*  *Commissioner of Patents and Trademarks*